US005415672A

United States Patent [19]

Fahey et al.

[11] Patent Number: 5,415,672

[45] Date of Patent: May 16, 1995

[54] DELIVERY OF BENEFICIAL CLAVIBACTER MICROORGANISMS TO SEEDS AND PLANTS

[75] Inventors: Jed W. Fahey, Columbia, Md.; Joanna Anders, Greenbelt, both of Md.

[73] Assignee: Crop Genetics International Corporation, Columbia, Md.

[21] Appl. No.: 171,774

[22] Filed: Dec. 22, 1993

Related U.S. Application Data

[63] Continuation of Ser. No. 10,510, Jan. 28, 1993, abandoned, which is a continuation of Ser. No. 793,300, Nov. 14, 1991, abandoned, which is a continuation of Ser. No. 474,647, Feb. 2, 1990, abandoned, which is a continuation of Ser. No. 368,167, Jun. 16, 1989, abandoned, which is a continuation of Ser. No. 194,247, May 16, 1988, abandoned, which is a continuation-in-part of Ser. No. 51,637, May 20, 1987, abandoned.

[51] Int. Cl.[6] .......................... A01C 1/06; A01C 1/08; A01N 63/00

[52] U.S. Cl. .................................. 47/57.6; 47/57.605; 47/57.613; 47/57.614; 47/57.615; 47/57.618; 435/172.3; 424/93.4

[58] Field of Search ........... 47/57.605, 57.613, 57.614, 47/57.615, 57.618, 57.6; 435/172.3; 424/93.4

[56] References Cited

U.S. PATENT DOCUMENTS

| | | | |
|---|---|---|---|
| 674,765 | 5/1901 | Hartleb | 71/77 |
| 2,932,128 | 4/1960 | Porter et al. | 47/58 |
| 2,954,643 | 10/1960 | Porter et al. | 47/58 |
| 2,995,867 | 8/1961 | Burton | 47/1 |
| 3,054,219 | 9/1962 | Porter et al. | 47/1 |
| 3,069,809 | 12/1962 | Simmons | 47/57.5 |
| 3,168,796 | 2/1965 | Scott et al. | 47/58 |
| 4,223,007 | 9/1980 | Spence | 424/93 |
| 4,277,462 | 7/1981 | Strobel | 424/93 |
| 4,291,497 | 9/1981 | Manankov | 47/58 |
| 4,367,609 | 1/1983 | Lloyd | 47/57.6 |
| 4,407,956 | 10/1983 | Howell | 47/1 R |
| 4,434,231 | 2/1984 | Jung | 47/57.6 |
| 4,517,008 | 5/1985 | Strobel et al. | 71/77 |
| 4,678,669 | 7/1987 | Ricard | 47/58 X |
| 4,798,723 | 1/1989 | Dart et al. | 47/57.6 X |
| 4,828,999 | 5/1989 | Jackson | 47/57.6 X |

FOREIGN PATENT DOCUMENTS

| | | | |
|---|---|---|---|
| 0125468 | 5/1984 | European Pat. Off. | 435/172 |
| 725592 | 4/1980 | U.S.S.R. | 47/58 |

OTHER PUBLICATIONS

Davis et al. 1984. International Journal of Systemic Bacteriology 34:107–117.
Nester et al. 1984. Ann. Rev. Plant Physiol. 35:387–413.
Davis et al. 1984. Plant Disease 68: 1095–1097.
Wastie, R. L., (1984) "Inoculating Plant Material by Jet Injection" *Plant Pathology* vol. 33 pp. 61–63.
Theodoroli, C. (1971) "Introduction of Mycorrhizal Fungi into Soil by Spore Inoculation of Seed" *Australian Forestry* vol. 35 pp. 23–26.
Davis, M. J. (1984) "Clavibacter: A New Genus . . . " *International Journal of Systematic Bacteriology* Apr. 1984, pp. 107–117.

(List continued on next page.)

*Primary Examiner*—David T. Fox
*Assistant Examiner*—Elizabeth C. Kemmerer
*Attorney, Agent, or Firm*—Finnegan, Henderson, Farabow, Garrett & Dunner

[57] ABSTRACT

A seed containing beneficial microorganisms, which, upon germination gives rise to a plant colonized by the microorganisms, and a method for producing the seed are provided. The seed is produced by adding the microorganisms to a biologically compatible liquid carrier to form a suspension of the microorganisms in the carrier, impregnating the seeds with the suspension, and removing the excess carrier from the seeds, whereby the viability of the microorganisms and the seeds is maintained. Plants colonized by beneficial microorganisms and methods of producing such plants are also disclosed.

4 Claims, No Drawings

OTHER PUBLICATIONS

Klein, T. M., et al. (1987) "High-Velocity Microprojectiles . . ." *Nature* vol. 327 pp. 70-73.

Berrie, A., et al., The Effect of Hydration-Dehydration on Seed Germination, New Phytol. 70: 135-142 (1971).

Chang, I., et al., Biological Control of Seedling Blight of Corn . . . , Phytopathology 58: 1395-1401 (1968).

Chao, W., et al., Colonization of the Rhizosphere by Biological Control Agents Applied to Seeds, Phytopathology 76: 60-65 (1986).

Dhingra, O., et al., Organic Solvent Seed Treater, Seed Sci. and Technol. 10: 105-108 (1982).

Dhingra, O., et al., Infusion of Fungicides Into Soybean Seeds with Intact Seed Coats . . . , Seed Sci. and Technol. 10: 109-117 (1982).

Esau, K., Anatomy of Seed Plants, Chap. 23 "The Seed", 455-473, John Wiley and Sons, New York (1977).

Goldsworthy, A., et al., Flash Imbibition: A Method for the Reinvigoration of Aged Wheat Seed, Seed Sci. and Tech. 10:55-65 (1982).

Goth, R., The Use of a Partial Vacuum to Inoculate Bean Seeds with Pathogenic Bacteria, Plant Disease Reporter 50: 110-111 (1966).

Hadar, Y., Evaluation of Trichoderma Koningii and T. harzianum from New York Soils . . . , Phytopathology 74: 106-110 (1984).

Hartman, J., et al., An Improved Method for the Inoculation of Corn with Erwinia spp., Phytopathology 63: 658-663 (1973).

J. Brockwell, et al., Relationship Between Viability and Avaibility of Rhizobium Trifolii Introduced Into Seeds of Rhizobium Trifolii . . . Aust, J. Agr. Res., 13, 1041-1053 (1962).

Microbial Technology, Henry J. Peppler Ed., Rheinhold Publishing Corp. New York, 1977, pp. 241-309.

Lewis W. Erdman, The Future of Preinoculated Seed, Seed World, 88 (5), 12-17 (1961).

R. Cooper, The Retention of P-Labeled Rhicobium by Legume Seed After Inoculation by Vacuum Treatment, Journal of Applied Bacteriology, 232-236 (1962).

R. A. Date et al., Vacuum Preinoculation Only Partly Effective, Crops Soils Mag., 14, 22 (1962).

Loneragan, et al. Nature 192, 526 (1961).

Leben, C., et al., Bacterial Pathogens: Reducing Seed and In Vitro Survival by Physical Treatments, Plant Disease 65: 876-878 (1981).

Mew, I., et al., Interaction Among Microorganisms Occurring Naturally and Applied to Pericarps . . . , Plant Dis. Reptr. 56: 861-863 (1972).

Norse, D., A Quantitative Inoculation Technique for Screening Sugarcane Varieties . . . , Plant Dis. Reptr. 57: 582-583 (1973).

O'Neill, N., et al., Infusion and Translocation of Systemic Fungicides Applied to Seeds in Acetone, Phytopathology 69: 690-694 (1979).

Rowell, J., et al., Factors Affecting the Partial Vacuum Inoculation of Seedling Corn with Ustilago Zeae, Phytopath. 43: 654-658 (1953).

Savino, G., et al., Effects of Presoaking Upon Seed Vigour and Viability During Storage, Seed Sci. and Technol. 7: 57-64 (1979).

Tao, K., et al., Practical Significance of the Application of Chemicals . . . , J. Amer. Soc. Hort. Sci. 99: 217-220 (1974).

Wallin, J., A New Method of Inoculating the Maydeae with Smut Fungi, Science 109: 312-313 (1949).

Seed Trade News, Technique Devised to Improved Productivity Without Fertilizer, 20-21, Oct. 15, 1986.

American Type Culture Collection "Catalogue of Bacteria and Phages".

Rolfe, B. G. &-Shine, J. (1984) Rhizobium-Leguminose symbiosis: The Bacterial Point of View. pp. 95-128 in Genes Involved in Microbe-Plant Interactions. Verma, D. P. S. & Hohn, T. Eds., Springer-Verlag, New York.

Easu, K. (1977) The Anatomy of Seed Plants, pp. 215-242, John Wiley & Sons, New York.

Verma, D. P. S. and Nadler, K. (1984) Rhizobium-Leguminose symbiosis: Host's Point of View. pp. 57-93 in Genes Involved in Microbe-Plant Interactions. Verma, D. P. S. & Hohn, T., Eds., Springer-Verlag, New York.

Frans J. deBruijn, The Unusual Symbiosis Between The Diazotropic Stem-Nodulating Bacterium Azorhizobium caulinodans ORS571 And Its Host, The Tropical Legume, Sesbania Rostrate, Symbiotic Nitrogen Fixation, 14, 457-504.

(List continued on next page.)

OTHER PUBLICATIONS

F. B. Dazzo and A. E. Gardiol, Host Specificity in Rhizobium-Legume Interal, 4—31 in Genes Involved in Microbe-Plant Interactions. Verma, D. P. S. & Hohn, T., Eds., Springer-Verlag, New York.

Peter B. Adams., "The Potential Of Mycoparasites for Biological Control Of Plant Diseases" *Annu. Rev. Phytopathol,* 28, (1990) pp. 59–72.

G. C. Papavizas, "Trichoderma and Gliocladium: Biology, Ecology, and Potential for Biocontrol" *Ann. Rev. Phytopathol,* 23, (1985) pp. 23–54.

R. C. Foster et al., "Plant Surfaces and Bacterial Growth: The Rhizosphere And Rhizoplane" *Phytopathogenic Prokaryotes,* vol. 1, pp. 159–185.

R. C. Foster, "The Ultrastructure of the Rhizoplane and Rhizosphere" *Ann. Rev. Phytopathol,* 24, (1986) pp. 211–234.

Ilan Chet, "Trichoderma-Application, Mode of Action, and Potential as a Biocontrol Agent of Soilborne Plant Pathogenic Fungi" *Trichoderma A Biocontrol Agent of Plant Fungi* (1987) pp. 137–160.

DELIVERY OF BENEFICIAL CLAVIBACTER MICROORGANISMS TO SEEDS AND PLANTS

This application is a continuation, of application Ser. No. 08/010,510, filed Jan. 28, 1993, now abandoned, which is a continuation of application Ser. No. 07/793,300, filed Nov. 14, 1991, now abandoned, which is a continuation of application Ser. No. 07/474,647, filed Feb. 2, 1990, now abandoned, which is a continuation of application Ser. No. 07/368,167, filed Jun. 16, 1989, now abandoned, which is a continuation of application Ser. No. 07/194,247, filed May 16, 1988, now abandoned, which is a continuation-in-part of application Ser. No. 07/051,637, filed May 20, 1987, now abandoned.

BACKGROUND OF THE INVENTION

This invention relates to methods for delivering beneficial microorganisms to seeds and plants and to seeds and plants containing such microorganisms. More particularly, the invention relates to seeds and plants containing viable beneficial microorganisms, methods for introducing such microorganisms into seeds and plants, and methods for colonizing plants with beneficial microorganisms by introducing the microorganisms into the seeds and plants.

It is a well-known fact that many types of microorganisms are harmful to seeds and plants. However, many types of microorganisms are also beneficial to plants. Nitrogen-fixing bacteria, such as Rhizobium spp., colonize the roots of legumes and provide nitrogen in a form usable by those plants. Certain other microorganisms, known as biological control agents, appear to provide some seeds and plants with a degree of protection against harmful microorganisms, when they are associated with those seeds and plants. For example, it has been shown that Trichoderma spp. can sometimes protect seeds as effectively as chemical fungicides when coated onto the seeds. Chao, et al., *Phytopathology*, 76:60–65 (1986). Still other microorganisms, such as the hybrid agricultural-chemical-producing endosymbiotic microorganisms disclosed in U.S. patent application Ser. No. 08/178617, which is incorporated herein by reference in its entirety, colonize the interior of plants in a symbiotic manner and provide useful agricultural chemicals, such as pesticides, to them.

Colonization of plants and seeds with beneficial microorganisms has conventionally been accomplished by applying the microorganisms directly to the surface of the seeds or to the soil surrounding the plants. With Rhizobium, for example, the microorganisms are usually coated onto the seeds, and they colonize the roots and rhizosphere of the plants as the plants emerge from the seeds. See U.S. Pat. No. 4,434,231 to Jung, U.S. Pat. No. 4,367,609 to Lloyd, U.S. Pat. No. 3,054,219 to Porter et al., and U.S. Pat. No. 2,995,867 to Burton. Similarly, the biocontrol agent Trichoderma is applied by coating it onto seeds. See Chao et al., supra, and Hadar et al., *Phytopathology*, 74:106–110 (1984). Alternatively, beneficial microorganisms have been applied to plants by preparing a water-based suspension of the microorganisms and spraying that suspension onto the plants or applying it directly to the soil around the plants. All of these methods have been used to colonize the surface, as opposed to the interior, of plants with beneficial microorganisms.

Seed coating and soil application techniques have at least two disadvantages. First, certain microorganisms will not survive well in the soil and will not colonize the roots or other parts of the plant as it emerges from the seed, unless the plant is mechanically or otherwise wounded to provide an entry to the microorganisms. Therefore, merely coating these microorganisms onto seeds will not cause colonization of the resultant plant. Second, even for microorganisms which can colonize plants by virtue of being applied to the surface of the seeds, there can be a natural loss of viability of some of the microorganisms and the efficiency of the colonization can be low.

The present inventor undertook to develop a method of colonizing plants and seeds with beneficial microorganisms that would overcome these disadvantages. It was known that pathogenic microorganisms could be impregnated into seeds by preparing an aqueous suspension of the pathogens, mixing the seeds with the pathogens, and using the technique of vacuum infiltration to force the pathogens into the seeds. See Leben, *Plant Disease*, 65:876–878 (1981) and Goth, *Plant Disease Reporter*, 50:110–111 (1966). Pathogenic microorganisms have also been inoculated into plants by vacuum infiltration (Rowell and DeVay, *Phytopathology*, 43:654–658 (1953)) and by means of a needleless medical jet injector (Wastie, *Plant Pathology*, 33:61–63 (1984)). However, such techniques lead to the destruction of the seed or the resultant plant by the pathogen.

The present inventor has discovered that beneficial microorganisms can be impregnated into seeds, whereby the microorganisms and seeds remain viable and the resulting plants are viable and colonized by the microorganisms. This is surprising in view of the fact that certain microorganisms, which are not themselves pathogenic to a particular plant species, can attack and destroy seeds of that species either pre- or post-harvest, while not causing disease in the plant itself. The present inventor has also discovered that certain beneficial microorganisms, which might have been expected to colonize plants by merely being applied to the surface of the plants, need to be physically injected into or otherwise caused to enter the plants for colonization to occur. The inventor has developed various techniques to implement these discoveries.

SUMMARY OF THE INVENTION

As demonstrated in the Description of the Preferred Embodiments, below, the present invention involves, inter alia, methods for introducing beneficial microorganisms into seeds and plants to obtain plants colonized by those microorganisms. This invention provides a means to overcome, for the first time, the shortcomings of the existing microorganism delivery technology as outlined above.

It is accordingly, one object of the present invention to provide a method for introducing beneficial microorganisms into seeds.

Another object of the present invention is to provide a seed containing beneficial microorganisms.

Still another object of this invention is to provide a method for colonizing plants with beneficial microorganisms.

A further object is to provide plants colonized by beneficial microorganisms.

Additional objects and advantages of the invention will be set forth in part in the description which follows and in part will be obvious from the description or may be learned by practice of the invention. The objects and advantages of the invention will be attained by means of the instrumentalities and combinations particularly pointed out in the appended claims.

To achieve the objects and in accordance with the purpose of the invention, as embodied and broadly described herein, the present invention provides a seed having beneficial microorganisms impregnated therein, which gives rise after germination to a plant colonized by the microorganisms. Preferably, the microorganisms are ones which, when metabolically active, are unable to colonize the plant unless introduced into the plant or its seed. Most preferably, the microorganisms are a strain selected from the genus Clavibacter, including ones which have been genetically engineered or otherwise modified to enhance or add desired characteristics.

The present invention also provides a method for introducing beneficial microorganisms into seeds by adding the microorganisms to a biologically compatible liquid carrier to form a suspension of the microorganisms in the carrier, impregnating the seeds with the suspension, and removing the excess carrier from the seeds, whereby the viability of the microorganisms and the seeds is maintained. In one preferred embodiment, the biologically compatible liquid carrier comprises a solution of water and a water soluble gum. In another preferred embodiment, the biologically compatible liquid carrier is a substantially anhydrous organic solvent and the microorganisms are dormant.

The present invention also provides a method for obtaining plants colonized by beneficial microorganisms and the plants so produced by adding the microorganisms to biologically compatible liquid carrier to form a suspension of the microorganisms in the carrier impregnating the seeds with the suspension, and growing the seeds to obtain the plants.

The present invention further provides a method for introducing beneficial microorganisms into plants and the plants so produced by adding the microorganisms to a biologically compatible liquid carrier to form a suspension of the microorganisms in the carrier and introducing the carrier into plants.

DESCRIPTION OF THE PREFERRED EMBODIMENTS

Reference will now be made in detail to the presently preferred embodiments of the invention, which, together with the following examples, serve to explain the principles of the invention.

The present invention relates to seeds and plants containing beneficial microorganisms. The microorganisms are generally, but not necessarily, dormant (i.e., alive, but metabolically inactive) in the seeds. The seeds are capable of germinating and growing into mature plants without being significantly adversely affected by the microorganisms. Upon germination, the seeds give rise to a plant colonized by the microorganisms. Thus, the viability of the microorganisms and the seeds are maintained.

Virtually, any type of seed may be used in the present invention. These include seeds of both monocotyledonous and dicotyledonous plants that may be useful for agronomic, horticultural, or ornamental purposes. Particularly, important groups of plants that provide seeds for the present invention are the cereals and grasses. The cereals include, but are not limited to, wheat, triticale, barley, rye, rice, and oats. The grasses include the sod and forage grasses, such as brome grass, blue grass, tall fescue grass, and Bermuda grass. Other grasses are the tropical grasses, such as sugar cane, corn, milet, and sorghum. Solanaceous plants, such as potatoes, tomatoes, tobacco, eggplant, and pepper are appropriate plant and seed hosts, as are brassicaceous plants, such as cauliflower, broccoli, cabbage, kale, and kohlrabi. Other suitable plant and seed hosts include carrots, parsley, sugar beets, cotton, fruit trees, berry plants, and grapes. In addition, the seeds and plants of the present invention include tree species, such as pine, spruce, fir, aspen and the various hardwoods. Seeds of the Gramineae, Leguminosae, and Malvaceae families are preferred. Particularly preferred seeds are those for corn, soybeans, rice, and cotton.

The microorganisms are any beneficial microorganisms that are capable of colonizing any plant for which this is desirable. They may be naturally occurring, genetically engineered, or the products of mutagenesis and selection.

The term "microorganisms" as used herein encompasses bacteria, fungi (including yeast), algae, and viruses. The term "bacteria" as used herein encompasses bacteria, bacteria-like organisms, and their equivalents, including actinomycetes.

The term "beneficial" as used herein refers to microorganisms which, on balance, provide a greater benefit to the plant than any harm they may cause. The determination of whether such a microorganism will benefit the plant can be made by those skilled in the art by considering any one or more of a multitude of factors. These include: 1) rendering nutrients more available or in greater amounts; 2) enhancing or inducing resistance to pathogens; 3) producing a desired chemical, such as a pesticide, itself or by conversion of plant metabolites; 4) conferring or enhancing stress tolerance; 5) increasing metabolic efficiency, such as photosynthetic efficiency, and 6) inactivating toxins.

The term "colonized" and similar terms refers to the presence of the microorganisms on, within, or in the immediate environment of any part of the plant. For example, the microorganisms can colonize the vascular system of the plants as in the case of certain hybrid endosymbiotic microorganisms described in U.S. application Ser. No. 08/178617 can colonize the rhizosphere of the plants as in the case of Rhizobium, or can colonize leaf surfaces of the plants as in the case of ice-nucleating pseudomonads.

In a preferred embodiment, the microorganisms are ones which, when metabolically active, are unable to colonize the plant when simply applied to the surface of the plant or seed or to the surrounding soil. These microorganisms can colonize the plant in a significant degree only when introduced into the interior of the plant or its seed.

The microorganisms may be genetically engineered to enhance one or more of their desirable characteristics or to add a characteristic that they do not naturally have. As used herein, the term "genetically engineered" and similar terms refers to microorganisms which have been manipulated by human intervention to delete DNA or RNA from their genome, rearrange DNA or RNA in their genome, or add DNA or RNA, including DNA or RNA from a different organism, to their genome through techniques including, but not limited to, recombinant DNA, recombinant RNA, cell fusion, conjugation, plasmid transfer, transformation, transfection, transduction, and microinjection.

Preferably, they are engineered to produce a chemical that they do not naturally produce or produce to any significant degree. The chemical will preferably be an agricultural chemical; that is, a chemical useful in plant agriculture. These include, but are not limited to, pesticides, antibiotics, plant growth regulators, fertilizers, and chelators, such as siderophores. The pesticides include insecticides, nematicides, miticides, herbicides, antiviral agents, and antifungal agents.

Conventional techniques of mutagenesis and selection can be applied to naturally occurring microorganisms to enhance one or more of their desired characteristics. For example, the techniques can be used to enhance their ability to colonize the interior of a plant or to act as a biocontrol agent. Thus, seeds and plants which contain such microorganisms are also within the scope of the present invention.

Endophytes, that is, microorganisms capable of entering into an endosymbiotic relationship with a plant host, are particularly useful in the present invention because they can be gentically engineered to produce an agricultural chemical as described in U.S. patent application Ser. No. 08/178617. Certain endophytes may also act as biological control agents. Whether or not a microorganism is an endophyte is determined with regard to a particular plant host. That is, it may be a pathogen for one plant and an endophyte for another.

Preferred naturally occuring endophytes are bacteria of the genus Corynebacterium or Clavibacter. *Clavibacter xyli* subsp. *cynodontis* and *Clavibacter xyli* subsp. *xyli* are particularly preferred. When the endophyte is a species of the genus Clavibacter, it is preferred that the plant be of the Gramineae, Leguminosae, or Malvaceae families. In this case, particularly preferred plants include corn, sorghum, sugar cane, and Bermuda grass. A particularly preferred strain of *Clavibacter xyli* subsp. *cynodontis* is the one on deposit with the American Type Culture Collection, 12301 Parklawn Drive, Rockville, Md. 20852 U.S.A. under Accession No. 33973.

The methods of the present invention are particularly useful for the endophyte *Clavibacter xyli* subsp. *cynodontis* because it has been discovered that this endophyte does not colonize its host plants unless it is deliberately introduced through openings in the surface of the plant. In addition, this endophyte does not colonize its host plant by being in the vicinity of the roots. Therefore, conventional seed coating technology cannot be used as a means of delivering the endophyte to the plant.

The microorganisms used the in present invention can also be biological control agents, such as *Bacillus subtilis, Chaetomium globosum*, Trichoderma spp., and Pseudomonas spp. These agents appear to exert their biological control activity by colonizing the rhizosphere of the developing plant and either acting in an antagonistic manner toward endogenous microflora or producing plant growth regulating compounds.

The microorganisms used in the present invention also encompass those that fix nitrogen. These include microorganisms of the genera Rhizobium, Bradyrhizobium, and Frankia.

Unlike the case with conventional seed coating technology, the microorganisms of the present invention are inside of the outer, protective seed coat (pericarp or testa). Moreover, experiments with both corn and soybean seed indicate that, at least for the endophyte *Clavibacter xyli* subsp. *cynodontis*, the microorganisms must be in the embryo itself for the resulting plant to be colonized.

The microorganisms of the present invention may be microencapsulated with a suitable food source which will enhance the microorganisms's ability to survive within the seed until such time that the germinating seed is capable of providing food to the microorganism. Such food source includes, but is not limited to, dehydrated culture medium; components of same, such as for example, cysteine and bovine serum albumin; and complex carbohydrate or amino acid sources, such as, for example, milk, starch or yeast extract. The food source and microorganism may be encapsulated through freeze-drying, spray-drying, liposome entrapment or other techniques that would be familiar to one of ordinary skill in the art. Such microencapsulation may increase the shelf life of the impregnated seeds.

The seeds of the present invention also encompass seeds containing beneficial microorganisms that are able to colonize the emerging plant when they are coated only on the outer surface of the seed, when such colonization occurs more efficiently, more rapidly, or in higher numbers when the microorganism is within the pericarp itself. Such microorganisms include those of the genera Rhizobium, Bradyrhizobium, Frankia, Trichoderma, Chaetomium, Pseudomondas, and Bacillus.

In the seeds of the present invention, the microorganisms preferably are dormant. That is, they are alive, but are metabolically inactive. They may be in the form of spores. They become reactivated when moisture is applied, as when the seeds are planted or otherwise germinated.

The seeds of the present invention are produced by:

(1) adding beneficial microorganisms to a biologically compatible liquid carrier to form a suspension of the microorganisms in the carrier; and (2) impregnating the seeds with the suspension or otherwise introducing the suspension into the seeds. Preferably, the excess suspension or carrier is removed from the seeds, such as by evaporation. This process is accomplished in such a way that the viability of the microorganisms and the seeds is maintained, so that the seeds are capable of germinating and the microorganisms are capable of colonizing the resulting plant.

The microorganisms can be in any culture medium that permits growth or sustains viability. Preferably, the cultures are substantially pure, that is, substantially free of unwanted microorganisms.

The biologically compatible liquid carrier is any liquid in which the microorganisms can form a suspension and which is not lethal to either the microorganisms or the seeds. This includes water and a water-based buffer, such as phosphate buffered saline. The suspensions are formed by adding cultures of the microorganisms to the liquid carrier and mixing microorganisms with the carrier and by related techniques known to persons skilled in the art.

In a preferred embodiment, the biologically compatible liquid carrier comprises a solution of water and a water-soluble gum. Such gums may be natural or synthetic. They include gelatin, sodium alginate, gum ghatti, xanthan gum, karaya gum, DOW-CORNING 1944A/B POLYMER PRODUCT (a silicone oil made by Dow-Corning), polyethylene oxide, NATROSOL™ product (a hydroxyethyl cellulose made by Hercules Chemical Co.), tragacanth gum, guar gum, gum arabic, locust bean gum, methylcellulose, carboxymethylcellulose, starch, and RHOPLEX™ B-15 product (an aqueous acrylic emulsion made by Rohm &

Haas). Methylcellulose, carboxymethylcellulose, xanthan gum, and RHOPLEX TM B-15 product are particularly preferred. These gums appears to act as a drying and preserving agent for the microorganisms as well as binding them to microscopic cracks within the seed or to intracellular spaces. They are preferably used in a concentration from about 0.1% to about 10% weight per volume of water.

After the microorganisms have been impregnated into the seeds, it is preferable that the excess suspension and carrier be removed. When the liquid carrier is an anhydrous organic solvent, drying may be accomplished rapidly at ambient temperature. When the liquid carrier contains water, the seeds are dried and careful selection of the dry-down temperature by means known to those of ordinary skill in the art is beneficial. The drying causes the microorganisms to become dormant. When the gum is used, it appears to act as a matrix in which enough moisture is removed so that the microorganisms become dormant yet enough moisture is maintained so that they remain viable.

The liquid carrier may also contain a buffer, which assists in maintaining the viability of the microorganisms, and surfactants, such as TWEEN 20 product (polyoxyethylenesorbitan monolaurate), TWEEN 40 product (polyoxyethylenesorbitan monopalmitate), TWEEN 60 product (polyoxyethylenesorbitan monostearate), TWEEN 80 product (polyoxyethylenesorbitan monooleate), TWEEN 85 product (polyoxyethylenesorbitan trioleate), REGULAID product (polyoxyethylenepolypropoxypropanol and alkyl-2-ethoxy ethanol dihydroxy propane), and SURFEL product (83% paraffin-based petroleum oil; 15% polyol fatty acid esters and polyethoxylated derivatives and 2% unidentified components). The surfactants aid in permitting the suspension of the microorganisms and the carrier to penetrate microscopic cracks and fissures in the hard, outer seed coat so that the microorganisms end up within that coat. Organic solvents and penetrants such as dimethyl sulfoxide (DMSO) or N,N-dimethyl formamide (DMF), also promote colonization, probably by nature of their unique properties as universal solvents and their ability to reduce surface tension. Particularly preferred concentrations are 1% DMSO or 3% DMF. In addition, chemicals such as fungicides can be added to the liquid carrier, if they are not lethal to the microorganisms. The toxicity of the fungicides can be determined by the person skilled in the art on a case-by-case basis. For example, *Clavibacter xyli* subsp. *cynodontis* has been found to tolerate significant levels of certain fungicides.

In an alternative embodiment, the biologically compatible liquid carrier is a substantially anhydrous organic solvent. Most organic solvents are toxic to metabolically active microorganisms. In such cases, the microorganisms should be dormant, and the organic solvent should be substantially anhydrous because water could cause microorganisms to reenter the active state. Microorganisms can be made dormant before being added to the solvent by conventional techniques. Lyophilization is preferred.

Virtually any organic solvent, which is nontoxic to the seed or the dormant microorganisms and which maintains the dormancy of the microorganisms, may be used. These include acetone, dichloromethane, trichloromethane (chloroform), carbon tetrachloride, DMSO, DMF, methanol, ethanol, benzene, n-hexane, cyclohexane, ortho-, meta-, and para-xylene, isopropanol, and n-butanol. Volatile organic solvents are particularly preferred because they have the advantage of being easily evaporated at the end of the process.

Various oils have also been found to be useful as organic solvents. These include vegetable, mineral, linseed, and silicone oil. The oils are relatively inert and nontoxic to the microorganisms and the seeds.

The parameters of the impregnation process, including type of liquid carrier, presence and concentration of surfactants, solvents and penetrants, may in light of the specification, be varied on a case-by-case basis depending on the variety of seed or plant, by means known to one of ordinary skill in the art to optimize the impregnation process. For example, in a preferred embodiment, a 3% aqueous solution of DMF may yield increased colonization efficiency in both field and sweet corn.

The seeds are impregnated with the microbial suspension in several different ways. One method involves applying the suspension to the seeds or mixing the suspension with the seeds and applying a vacuum according to the technique of Goth, supra, incorporated herein by reference. At the end of the evacuation, the system is allowed to rapidly repressurize, and the suspension is drawn into the seeds. The degree of the vacuum and the length of time it is applied can be determined by a person skilled in the art in view of the teachings herein. A preferred time period for evacuation is at least about 1 hour. A particularly preferred period of time is 40 minutes for corn. When this technique is used with the water-based systems, the seeds may be presoaked to enhance the ease of penetration by the suspension. It is preferable that some seeds, for example, corn, are presoaked or imbibed overnight (approximately 17 hours) or for one day.

A second method of impregnating the seeds with the suspension involves applying the suspension to the seeds or otherwise mixing the seeds and the suspension and then applying pressure. The degree of pressure and the length of time it is applied can be determined by a person skilled in the art in view of the teachings herein. In the pressure treatment, any gas may be used but in preferred embodiments, $O_2$ and $N_2$ may be used.

In a third technique, seeds are impregnated by applying the suspension to the seeds or otherwise mixing the seeds and the suspension and then subjecting the seeds and suspension to centrifugation. In an alternative embodiment, the suspension of microorganisms is mixed with the seeds, and then the suspension and seeds can be centrifuged while under pressure or vacuum. The specific pressure differential used can be determined by one of ordinary skill in the art in light of the teachings herein. The speed and length of centrifugation can be determined by a person skilled in the art in view of the teachings herein.

A fourth technique involves the forceful injection of the suspension into the seeds. This can be done with a needle and syringe, a medical needleless jet injector, or by coating the suspension onto high velocity microprojectiles and propelling projectiles into the seeds with sufficient force to cause them to penetrate the coat. It can also be done by puncturing the coat with a solid needle.

Needleless injection is accomplished by propelling a small amount (from about 10 to about 1000 microliters) of microorganisms suspended in a liquid carrier through a small jet or orifice under very high pressure. The stream of liquid remains coherent over a short distance and "punctures" a hole for itself in a solid substrate.

Any number of these injectors, which have been developed for the medical products industry, can be used to propel microorganisms into seed and plant tissue according to the methods of the present invention.

The microprojectile technique is disclosed in Klein et al., Nature, 327:70–74 (1987), which is incorporated herein by reference. With the microprojectiles, it is also possible to coat a culture of the microorganisms directly onto, or place the microorganisms into, the microprojectiles without first suspending them in the biologically compatible liquid carrier.

A variation of the injection technique is to use a solid needle or other sharp instrument to puncture the pericarp and then use vacuum or pressure infiltration or simply permit the punctured seed to come in contact with the suspension.

For certain embodiments of the present invention, it is preferable, but not necessary, to use vacuum or pressure infiltration or the various means of forcefully injecting the suspension. The carrier need only be applied to the seeds and allowed to remain in contact with the seeds for a period of time sufficient for the carrier to naturally penetrate the seed coat and bring the microorganisms into the seed. For some embodiments of the invention, it is preferable, but not necessary, to add a finely divided inorganic solid, such as diatomaceous earth, microparticulate glass, or carborundum, to the suspension to cause "cracks" which enhance penetration of the beneficial organisms.

After the seeds have been impregnated with the microbial suspension, the seeds are recovered. Preferably, the excess suspension and/or carrier is removed. When the liquid carrier contains water or a volatile organic solvent, the water or solvent is allowed to evaporate before the seeds are stored. The evaporation may be assisted by drying of the seeds by various means known to those skilled in the art. The seeds may be planted or otherwise germinated immediately or stored until germination is desirable. If stored, it is preferable that the seeds be stored at controlled levels of humidity. It is within the skill of one of ordinary skill in the art to select the humidity for storage to maintain optimum viability.

The method of the present invention may be practiced without taking special precautions to prevent seed contamination by undesirable or harmful microorganisms. However, it is preferred that contamination be controlled by fungicides or other conventional seed treatments applied, for example, via coating, pelleting, or film-coating, in order to prevent seed or plantlet damage.

This invention also relates to a method for introducing beneficial microorganisms directly into a plant itself instead of via the seed. While it has been known that pathogens can be directly introduced into plants, the present inventor has determined that certain beneficial microorganisms, particularly certain endophytes, need to be directly introduced into the plant, such as by injection, in order to colonize the plant. The inventor further discovered that such introduction can be done with limited or no injury to the plant. The preferred use of this method is for microorganisms that can only enter the plant by being placed or forced through the outer surface of the plant and into the interior of the plant. An example of such a microorganism is the bacterial endophyte Clavibacter xyli subsp. cynodontis. However, any of the previously mentioned microorganisms can be used.

The method comprises adding the microorganisms to a biologically compatible liquid carrier to form a suspension of the microorganisms in the carrier and impregnating or injecting the plants with the suspension. The biologically compatible liquid carrier is culture medium, water, or any of the previously mentioned carriers.

The suspension is impregnated into the plants using any of the techniques mentioned herein. Vacuum and pressure infiltration are most conveniently used with seedlings. Injection with needleless medical injectors, or microprojectiles is more conveniently done with more mature plants. The needleless injection technique is disclosed in Wastie, Plant Pathology, 3:61–64 (1984), which is incorporated herein by reference.

In an alternative embodiment, the suspension is introduced into the plant by mixing it with a surfactant and placing the mixture onto an appropriate structure, such as the apex of the plant. See Hartman and Kelman, Phytopathology 63:658–663 (1973), which is incorporated herein by reference.

It is to be understood that the application of the teachings of the present invention to a specific problem or environment will be within the capabilities of one having ordinary skill in the art in light of the teachings contained herein. Examples of the products of the present invention and the processes for their production appear in the following examples.

EXAMPLE 1

Preliminary experiments were conducted using surface sterilized seeds which were treated with pure cultures of bacteria and planted axenically in sterile containers. The experiments demonstrated colonization efficiencies of up to 100% when soybean (Glycine max) seed was vacuum infiltrated with a strain of Clavibacter xyli subsp. cynodontis (Cxc) in dilute solutions of dimethyl sulfoxide (DMSO) and up to 43% when vacuum infiltrated with dilute solutions of N,N-dimethyl formamide (DMF).

EXAMPLE 2

One hundred and fifty seeds of soybean cultivar "Pella" were placed in a suspension containing $10^9$ colony-forming units per milliliter (CFU/ml) of a 5–7 day old culture of the endophytic bacterium Cxc in 100 mls of 3% DMF in standard phosphate buffered saline (PBS) (an aqueous solution of $KH_2PO_4$ at 0.45 g/l, $K_2HPO_4$ at 1.16 g/l, and NaCl at 8.5 g/l) at room temperature. Control seeds were treated similarly except that DMF was left out of the PBS solution. The vessels containing immersed seeds were then subjected to a vacuum of 70 mm Hg. The vacuum was maintained for a period of one hour, during which, at three separate times, the vacuum was rapidly released from the chamber, immediately followed by re-evacuation. All seeds were removed immediately after vacuum infiltration, air-dried at ambient temperature in a forced air seed dryer for one hour, and planted within 3 hours in METRO-MIX TM product (manufactured by W. R. Grace Co.) potting medium in a greenhouse so that the bacterial colonization of the resultant plantlets could be evaluated.

Plants were harvested 23 days after seed planting and bioassayed for the presence of the endophyte Cxc. Germination was in the range of 70–90% for all treatments and controls. Colonization of the plants derived from DMF treated seed was 48% compared to 7% for controls treated with PBS alone.

EXAMPLE 3

Seeds of the corn genotype FR632, obtained from Illinois Foundation Seeds, Inc., Champaign, Ill., were imbibed (soaked) in PBS at low temperature (16° C.), in the dark, for a period of 3 days. This imbibition softened the seed tissue and permitted the introduction of a needle into the seed. After 3 days of imbibition, a high concentration of Cxc was introduced directly into the embryo portion of the seed by stabbing with the needle.

The seeds were then placed in a suspension containing $10^9$ CFU/ml of Cxc in PBS at room temperature and vacuum infiltrated as in Example 2. The seeds were removed immediately after vacuum infiltration, air-dried at ambient temperature, and planted within 4 hours in METRO-MIX TM product potting medium in a greenhouse so that the bacterial colonization of the resultant plantlets could be evaluated.

Plants were harvested 28 days after seed planting and bioassayed for the presence of the endophyte. One hundred percent of the plants which developed were colonized.

EXAMPLE 4

Seeds of the corn genotype FR632 were surface sterilized by rinsing for less than one minute in 70% ethanol followed by 15 minutes in 50% CLOROX TM PRODUCT with 300 mg. per liter ALCONOX TM (manufactured by Alconox Inc.) detergent. The CLOROX TM product was rinsed off exhaustively with sterile distilled water. The seeds were then aseptically placed in a suspension containing $10^9$–$10^{11}$ CFU/ml of Cxc suspended in a bacterial culture medium. A sharp needle was then used to stab the embryo portion of the seeds while holding them totally submerged under the surface of the liquid. A vacuum of 700 mm/Hg was then drawn on the container in which the seeds and bacterial solution were held and maintained for 2.5 hours as in Example 2, except all handling was done aseptically. The seeds were removed immediately after vacuum infiltration and either planted directly or coated with a 1:10 dilution in talc of commercially available CAPTAN TM 50WP (manufactured by Stauffer, sold by Meyer Seed Co.) followed immediately by planting. Planting was into sterile tubes containing PERLITE TM product growth support saturated with Hoagland's solution mineral nutrients.

Plants were harvested 36 days after seed planting and bioassayed for the presence of the endophyte. There was no difference between CAPTAN TM 50WP treated and non-treated seeds in either germination rate (75%) or endophyte colonization of the resulting plants (87%).

EXAMPLE 5

Seeds of the corn genotype FR632 were imbibed in PBS containing $10^9$–$10^{11}$ CFU/ml of the endophyte Cxc at low temperature (16° C.), in the dark. After 3 days of imbibition, $10^9 10^{11}$ CFU/ml of Cxc was introduced directly into the embryo portion of the seed by stabbing with a needle.

The seeds were then placed in a suspension containing about $10^9$ CFU/ml of Cxc in PBS at room temperature and vacuum infiltrated as in Example 2. Seeds were removed immediately after vacuum infiltration, air-dried at ambient temperature, coated with a 50% dilution (in talc) of a CAPTAN TM 50WP, and planted within 4 hours either in sterile tubes containing PERLITE TM product (manufactured by W. R. Grace Co.) growth support saturated with Hoagland's solution mineral nutrients or in METRO-MIX TM product potting medium in a greenhouse so that bacterial colonization of the resultant plantlets could be evaluated.

Plants were harvested 19 days after seed planting and bioassayed for the presence of the endophyte. One hundred percent of the plants which developed in sterile test tubes were colonized with the endophyte, and 33% of the plants which developed in the greenhouse were colonized.

EXAMPLE 6

Seeds of the cotton variety "DPL 50" and the soybean cultivar "Forrest" were placed in a suspension containing $10^{10}$–$10^{11}$ CFU/ml of Cxc in PBS at room temperature and vacuum infiltrated at very high vacuum (200 microns of Hg) for a period of about 1 hour. The seeds were removed immediately after vacuum infiltration, air-dried at room temperature, and planted immediately in sterile tubes containing PERLITE TM product growth support saturated with Hoagland's solution mineral nutrients so that bacterial colonization of the resultant plantlets could be evaluated.

Plants were harvested 16 days after seed planting and bioassayed for the presence of the endophyte. Eighty-three percent of the cotton and 54% of the soy plantlets which developed were colonized with the endophyte.

EXAMPLE 7

Seeds of the corn genotype FR632 were surface sterilized as in Example 4 and placed in solutions of $10^9$–$10^{11}$ CFU/ml of Cxc in (A) 1% NATROSOL TM product+1% CAPTAN TM 50WP product in water, (B) 1% NATROSOL TM product+1% CAPTAN TM 50WP in S8 nutrient bacterial growth medium, or (C) PBS. In addition, Cxc was injected into the embryo portion of half the seeds as in Example 4. All treated seeds were subjected to a pressure of 100 pounds per square inch (psi) for 1.5 hrs. The seeds were immediately removed and planted to sterile tubes as in Example 5.

Plants were harvested 31 days after seed planting and bioassayed for the presence of the endophyte. Although injection severely reduced germination (41% and 25% for injected seeds from A+B, respectively, compared to 91% for uninjected seeds from both A+B), colonization frequencies were excellent in most of the treatments:

| | |
|---|---|
| A - injected | 100% |
| A - not injected | 90% |
| B - injected | 100% |
| B - not injected | 72% |
| C - injected; whole treatment lost to contamination | |
| C - not injected | 57% |

EXAMPLE 8

Seeds of the corn genotype FR632 were imbibed in PBS at 16° C., in the dark, for 1 day followed by direct injection of Cxc into the embryo portion of the seeds. There was no subsequent vacuum or pressure infiltration of the seeds. In comparison to E only 1% of the resultant plants became colonized. Therefore, although vacuum or pressure infiltration is not essential for suc-

13 cessful colonization, it is extremely beneficial in most cases.

EXAMPLE 9

Seeds of *Glycine max* var. *Pella* were vacuum infiltrated, as in Example 4, for 1 hour with a suspension of $1.4 \times 10^8$ CFU/ml of Cxc in 1% methylcellulose and 1% Tween 20. The seeds were dried overnight and then planted in a greenhouse in METRO-MIX TM product so that the bacterial colonization of the resulting plants could be evaluated. Plants were harvested 33 days after planting and bioassayed for the presence of the endophyte. Colonization of the plants derived from treated seed was 23% with 70% seed germination.

EXAMPLE 10

Seeds of corn (FR632) and soybean (Pella) were treated by soaking for 2 hrs. in mineral oil, corn oil, silicone oil or RHOPLEX TM B-15 Emulsion. Seeds were then allowed to drip dry and planted in a greenhouse to assess germination. Germination rates assessed 12 days after planting were as follows:

| Treatment | Corn | Soy |
| --- | --- | --- |
| Untreated Control | 97% | 100% |
| Rhoplex B-15 Product | 89% | 76% |
| Mineral Oil | 23% | 90% |
| Corn Oil | 59% | 98% |
| Silicone Oil | 23% | 95% |

Treatment with certain oils will therefore not dramatically affect the germination of seeds.

Other experiments have demonstrated that Cxc can be stored at room temperature in each of these compounds for greater than month and remain viable.

EXAMPLE 11

Certain volatile organic solvents were examined for their effect on seed germination. Seeds of corn (FR632) and soybean (Pella) were treated by vacuum infiltration with these solvents as in Example 4 for 1 hour. Seeds were then air dried for an hour at room temperature and planted in METRO-MIX TM product in a greenhouse. Germination was assessed 10 days later (1–5) or 5 days later (6–12) (all numbers given as percent germination):

| Treatment | Corn | Soy |
| --- | --- | --- |
| (1) Untreated Control | 94 | 96 |
| (2) Acetone | 95 | 96 |
| (3) Carbon Tetrachloride | 90 | 98 |
| (4) Dichloromethane | 84 | 97 |
| (5) Chloroform | 89 | 88 |
| (6) Cyclohexane | | 75 |
| (7) Xylenes (o-, m-, & p-) | | 81 |
| (8) Linseed oil | | 66 |
| (9) n-Hexane | | 93 |
| (10) Isopropanol | | 79 |
| (11) n-Butanol | | 74 |
| (12) Ethyl Acetate | | 70 |

Other experiments have shown that the endophyte Cxc can survive treatments of greater than 1 hour soaking in these solvents, if the bacterium is lyophilized (freeze-dried) prior to being placed in the solvents.

EXAMPLE 12

A suspension of $10^9$ CFU/ml Cxc in PBS was loaded into the SYRIJET MARK III product medical injector as per the instructions of the manufacturer (Mizzy, Inc., Clifton Forge, Va. 24422). Aliquots of 500 microliters each were inoculated into 5-week old greenhouse-grown corn and 3-week old greenhouse-grown soy plants by holding the gun to the stem slightly above the soil line and pressing the trigger.

Plants were harvested 30 days after inoculation and bioassayed for the presence of the endophyte in the stem tissue of the plant. Ninety-six percent (96%) of the corn plants and 93% of the soybean plants inoculated in this manner became colonized with the endophyte.

EXAMPLE 13

Twenty-day old greenhouse-grown plants of the corn genotype FR632 were treated by placing a few drops of a suspension containing between $3-10^9$ CFU/ml of the Cxc in 1% Tween 20, 40, 60, 80, and 85 in the whorl (apex) of the plant.

Plants were harvested 35 days after inoculation and bioassayed for the presence of the endophyte in the stem tissue of the plant. The plants showed the following percent colonization: 90% (TWEEN 20 product), 33% (TWEEN 40 product), 54% (TWEEN 60 product), 34% (TWEEN 80 product), and 55% (TWEEN 85 product).

EXAMPLE 14

Seeds of the sweet corn variety "EARLIKING" product (provided by Meyer Seed Co.) and the field corn variety "DEKALB T1100" product (provided by DeKalb-Pfizer Genetics) were incubated in the dark at 16° C. The seeds were placed in beakers containing enough distilled, deionized water (DD-$H_2O$) to fully cover the seeds for imbibition. After 1, 3, 5 and 17 hrs of imbibition, the seeds were removed and placed in a solution of 3% DMF in PBS containing approximately $3 \times 10^9$ CFU/ml Cxc which had just been harvested from log phase growth on semi-solid medium. These immersed seeds were then immediately subjected to a pressure of 200 pounds/square inch (psi), with nitrogen as the pressurizing gas, for a period of 20 minutes. Seeds which had received no imbibition (dry) were also subjected to the above-described pressure inoculation treatment (P.I.). Following inoculation, seeds were dried in a forced air oven at 40° C. for 5.5 hr. (Earliking) or 3 hr. (T1100) and coated with CAPTAN 400D product (formulated by Gustafson). This treatment was applied at a rate of 1.2 ml. of a 7-fold dilution of formulated product, about 35% active ingredient, in water, per 150 seeds. After drying, seeds were planted in Metro-Mix TM potting medium in a greenhouse so that the bacterial colonization of the resultant plantlets could be evaluated. Plants were harvested about 2 months after planting and assayed for the presence of the endophyte Cxc. Assay was performed by squeezing the sap from the basal cut end of a surface-sterilized stem segment onto plates of semi-solid enrichment medium designed to selectively enhance the growth of Cxc over that of potential contaminants. The percent colonization rates were as follows:

| Variety | Pretreatment | % Colonization |
| --- | --- | --- |
| Earliking Product | dry | 0 |
| " | 1 hr imbibed | 0 |
| " | 3 hr imbibed | 6 |
| " | 5 hr imbibed | 17 |
| " | 17 hr imbibed | 93 |

-continued

| Variety | Pretreatment | % Colonization |
|---|---|---|
| T1100 | dry | 0 |
| " | 1 hr imbibed | 2 |
| " | 3 hr imbibed | 2 |
| " | 5 hr imbibed | 10 |
| " | 17 hr imbibed | 46 |

EXAMPLE 15

Seeds of the sweet corn varieties "HOW SWEET IT IS" product (from Crookham Co.) and "WHITE LIGHTNING" product (from Stokes Seeds Ltd.) were imbibed overnight (approximately 17 hr.) as in Example 14. Both the imbibed seeds and dry controls were then placed in a solution of 3% DMF in PBS containing $1 \times 10^{10}$ CFU/ml Cxc which had just been harvested from log phase growth on semi-solid medium. These immersed seeds were then immediately subjected to a vacuum inoculation treatment (V.I.) consisting of the application of a vacuum of 700 mm Hg for a period of 1 hr. The seeds were immediately drained and dried under forced air at about 23° C. for 1 hr. The seeds were coated with CAPTAN 50WP ™ product, planted in the greenhouse and evaluated as in Example 14.

| Variety | Pretreatment | % Colonization |
|---|---|---|
| How Sweet It Is Product | dry | 12 |
| " | 17 hr imbibed | 70 |
| White Lightning | dry | 0 |
| " | 17 hr imbibed | 71 |

EXAMPLE 16

Seeds of sweet corn variety EARLIKING product were imbibed for 17 hr. as in Example 14. The seeds were pressure inoculated with $1 \times 10^{10}$ CFU/ml of Cxc in either PBS, 3% DMF in PBS or 1% DMSO in PBS as in Example 14 and dried as in Example 15. The seeds were coated with CAPTAN 50WP ™, planted in the greenhouse and evaluated as in Example 14.

| Variety | Pretreatment | Treatment | % Colonization |
|---|---|---|---|
| Earliking Product | dry | 3% DMF | 36 |
| " | 17 hr imbibed | " | 83 |
| " | dry | PBS | 38 |
| " | 17 hr imbibed | " | 94 |
| " | dry | 1% DMSO | 60 |
| " | 17 hr imbibed | " | 90 |

EXAMPLE 17

Seeds in this experiment were inoculated and handled in a manner identical to Example 16, except that seeds were planted in the field in Howard County, Md. in August, 1987 with no irrigation. Evaluation was as in Example 14.

| Variety | Pretreatment | Treatment | % Colonization |
|---|---|---|---|
| Earliking | dry | 3% DMF | 38 |
| " | 17 hr imbibed | " | 88 |

EXAMPLE 18

Seeds of sweet corn variety "EARLIKING" product were inoculated with $63 \times 10^9$ CFU/ml Cxc in 3% DMF as in Example 16 except that compressed oxygen was also used to pressurize the treatment vessel. Seeds were handled and evaluated as in Example 16 except that they were dried overnight.

| Variety | Pretreatment | Treatment | % Colonization |
|---|---|---|---|
| Earliking | dry | 3% DMF; $O_2$ | 22 |
| " | 17 hr imbibed | " | 92 |
| " | dry | 3% DMF; $N_2$ | 21 |
| " | 17 hr imbibed | " | 87 |

EXAMPLE 19

Seeds of the sweet corn variety "EARLIKING" product and the field corn variety T1100 were imbibed and pressure inoculated with $1 \times 10^{10}$ CFU/ml of Cxc as in Example 16. They were dried overnight at 23° C. in a forced air stream for 5.5 hr (EARLIKING product) or 3 hr (T1100) at 40° C. All inoculated seeds were treated with fungicide, Captan 400D, and evaluated as in Example 14.

| Variety | Pretreatment | Treatment | Drying | % Colonization |
|---|---|---|---|---|
| Earliking Product | dry | 3% DMF | 23° C. | 6 |
| " | 17 hr imbibed | " | " | 95 |
| " | dry | PBS | " | 7 |
| " | 17 hr imbibed | " | " | 94 |
| " | dry | 1% DMSO | " | 2 |
| " | 17 hr imbibed | " | " | 91 |
| T1100 | dry | 3% DMF | " | 0 |
| " | 17 hr imbibed | " | " | 66 |
| " | dry | PBS | " | 0 |
| " | 17 hr imbibed | " | " | 64 |
| " | dry | 1% DMSO | " | 0 |
| " | 17 hr imbibed | " | " | 69 |
| Earliking Product | dry | 3% DMF | 40° C. | 4 |
| " | 17 hr imbibed | " | " | 89 |
| " | dry | PBS | " | 0 |
| " | 17 hr imbibed | " | " | 87 |
| " | dry | 1% DMSO | " | 0 |
| " | 17 hr imbibed | " | " | 96 |
| T1100 | dry | 3% DMF | " | 0 |
| " | 17 hr imbibed | " | " | 53 |
| " | dry | PBS | " | 0 |
| " | 17 hr imbibed | " | " | 52 |
| " | dry | 1% DMSO | " | 0 |
| " | 17 hr imbibed | " | " | 56 |

EXAMPLE 20

Seeds of the field corn variety FR632 and the sweet corn varieties "EARLIKING" product and "SENECA HORIZON" product (from Robson's Seed Farms), were pressure inoculated as in Example 14, except that pressure was applied for 30 min and was interrupted momentarily by three cycles of release followed immediately by re-pressurization. Seeds were dried overnight at 23° C., under a stream of forced air, coated with CAPTAN 50WP ™, planted in the greenhouse and evaluated as in Example 14.

| Variety | Pretreatment | Treatment | % Colonization |
|---|---|---|---|
| FR632 | 17 hr imbibed | 3% DMF | 28 |
| Earliking Product | 17 hr imbibed | " | 97 |
| Seneca Horizon Product | 17 hr imbibed | " | 77 |

EXAMPLE 21

Dry seeds of a number of varieties of corn (EARLIKING product, WHITE SUNGLOW product (from Meyer Seed Co.) and EARLY SUNGLOW Product (from Meyer Seed Co.)) were subject to pressure inoculation with $5 \times 10^9$ CFU/ml of Cxc in 3% DMF as in Example 14 except that the duration of pressure treatment was 1 hour. Seeds were dried overnight on a forced air seed drier, coated with CAPTAN 50WP TM, planted in the greenhouse and evaluated as in Example 14.

| Variety | Pretreatment | Treatment | % Colonization |
|---|---|---|---|
| Earliking | dry | 3% DMF | 20 |
| White Sunglow | " | " | 50 |
| Early Sunglow | " | " | 85 |

EXAMPLE 22

Seeds of four sweet corn varieties and one field corn variety were imbibed for 17 hrs. and inoculated by pressure (P.I.) or by vacuum (V.I.), using a 3% DMF solution. The experiment was conducted as in Example 15 (V.I.) except that where P.I. was used, it was applied as in Example 14.

| Variety | Pretreatment | Treatment | % Colonization |
|---|---|---|---|
| How Sweet It Is Product | 17 hr. imbibed | 3% DMF; V.I. | 12 |
| Early Sunglow Product | " | " | 8 |
| Earliking Product | " | " | 12 |
| Seneca Horizon Product | " | " | 4 |
| FR632 | " | " | 0 |
| How Sweet It Is Product | " | 3% DMF; P.I. | 68 |
| Early Sunglow Product | " | " | 92 |
| Earliking Product | " | " | 79 |
| Seneca Horizon Product | " | " | 84 |
| FR632 | " | " | 13 |

EXAMPLE 23

Seeds of five sweet corn varieties and one field corn variety were inoculated by either pressure or vacuum as in Example 22, except that Cxc was delivered in S8 bacterial culture medium rather than in 3% DMF.

| Variety | Pretreatment | Treatment | % Colonization |
|---|---|---|---|
| How Sweet It Is Product | 17 hr. imbibed | S8; V.I. | 12 |
| White Lightning Product | " | " | 9 |
| Earyl Sunglow Product | " | " | 3 |
| Earliking Product | " | " | 8 |
| Seneca Horizon Product | " | " | 0 |
| FR632 | " | " | 0 |
| How Sweet It Is Product | " | SB; P.I. | 48 |
| White Lighting Product | " | " | 81 |
| Early Sunglow Product | " | " | 83 |
| Earliking Product | " | " | 73 |
| Seneca Horizon Product | " | " | 68 |
| FR632 | " | " | 19 |

EXAMPLE 24

Seven field corn varieties and one sweet corn variety were inoculated by vacuum or pressure with Cxc in 3% DMF as in Example 22. However, seeds were first surface disinfected. Specifically, they were rinsed with 70% ethanol for 2 minutes, immersed in 40% CLOROX TM product with ALCONOX TM product detergent added as a wetting agent for 15 minutes, rinsed with at least 3 complete changes of sterile rinse water, and finally subjected to 15 minutes dry-down on absorbent paper in a laminar flow cabinet. The seeds were then inoculated. Following inoculation, seeds were dried down in a laminar flow cabinet for 1.5 hrs, treated with CAPTAN 50WP TM product, planted in sterile tubes containing PERLITE TM product and Hoagland's nutrient solution and incubated under artificial light at 28° C. After 2 weeks, seedlings were transplanted to pots in the greenhouse and processed and evaluated as in Example 14.

| Variety | Pretreatment | Treatment | % Colonization |
|---|---|---|---|
| (LH1 × H93)LH38 | surface disinfested | 3% DMF; P.I. | 85 |
| (Mol7 × LH58)A634 | surface disinfested | " | 77 |
| LH132 × LH51 | surface disinfested | " | 47 |
| A632 × LH39 | surface disinfested | " | 95 |
| LH38 × A632 | surface disinfested | " | 93 |
| FR632 | surface disinfested | " | 80 |
| T1100 | surface disinfested | " | 69 |
| Earliking Product | surface disinfested | " | 21 |
| (LH1 × H93)LH38 | surface disinfested | 3% DMF; V.I. | 0 |
| (Mol7 × LH58)A634 | surface disinfested | " | 0 |
| LH132 × LH51 | surface disinfested | " | 0 |
| A632 × LH39 | surface disinfested | " | 2 |
| LH38 × A632 | surface disinfested | " | 56 |
| FR632 | surface disinfested | " | 3 |
| T1100 | surface disinfested | " | 35 |
| Earliking Product | surface disinfested | " | 11 |

EXAMPLE 25

Seeds of field corn variety FR632 were vacuum inoculated with Cxc in either 3% DMF or S8 as in Example 24, except that vacuum was released and immediately re-applied at three times during the one hour vacuum inoculation period. Plants were evaluated for colonization by Cxc at 17 days, the time at which they were transferred out of test tubes and into the greenhouse and at 2 months following planting.

| Variety | Pretreatment | Treatment | Assay | % Colon-ization |
|---|---|---|---|---|
| FR632 | surface disinfestation | S8; V.I. | 17 d | 70 |
| " | surface disinfestation | 3% DMF; V.I. | " | 11 |
| " | surface disinfestation | S8; V.I. | 2 mo | 100 |
| " | surface disinfestation | 3% DMF; V.I. | " | 100 |

EXAMPLE 26

Seeds of corn variety FR632 were imbibed as in Example 14 for either 17 or 41 hrs, after which they were centrifuged for various periods of time in the presence of a solution of about $10^9$ CFU/ml of Cxc. Following this centrifugation, the seeds were dried, coated with CAPTAN 50WP™ product, planted and evaluated as in Example 15.

| Imbibition | Cxc Carrier | Centrifugation | % Colonization |
|---|---|---|---|
| 1 d | DD-$H_2O$ | 5 min | 5 |
| " | " | 10 min | 0 |
| " | " | 15 min | 8 |
| 2 d | | 5 min | 2 |
| " | " | 10 min | 22 |
| " | " | 15 min | 31 |
| 1 d | PBS | 5 min | 10 |
| " | " | 10 min | 11 |
| " | " | 15 min | 16 |
| 2 d | | 5 min | 45 |
| " | " | 10 min | 39 |
| " | " | 15 min | 21 |

EXAMPLE 27

Aqueous suspensions of three surfactants in DD-$H_2O$, containing $3.4\times10^9$ CFU/ml of Cxc were applied by pipet to the whorls of 13 day old corn plants (variety FR632) until drip. Plants were evaluated for colonization as in Example 14.

| Treatment | % Colonization |
|---|---|
| 1% Regulaid | 60 |
| 1% Tween 20 | 75 |
| 1% Surfel | 71 |
| DD-$H_2O$ control | 9 |

EXAMPLE 28

Two mls of a solution containing a surfactant in DD-$H_2O$, Cxc at about $5\times10^9$ CFU/ml was sprayed (using a hand-operated atomizer-type sprayer) into the whorls of developing corn (FR632) plants, in the greenhouse. Some plants were lightly dusted with 600 mesh carborundum (Carb.) powder immediately prior to spraying with Cxc. Plants were evaluated for Cxc colonization as in Example 14.

| | % Colonization When Inoculated At: | | | | | |
|---|---|---|---|---|---|---|
| Treatment | 1 WK | 2 WK | 3 WK | 4 WK | 5 WK | 9 WK |
| Untreated Control | 0 | 0 | 0 | 0 | 0 | 0 |
| 0% Surfel + Carb. | 0 | 0 | 44 | 30 | 20 | 0 |
| 0.1% Surfel + Carb. | 0 | 5 | 16 | 56 | 38 | — |
| 0.3% Surfel + Carb. | 0 | 15 | 35 | 33 | 20 | — |
| 0.5% Surfel + Carb. | 0 | 22 | 31 | 77 | 10 | — |
| 0.7% Surfel + Carb. | 41 | 32 | 32 | 58 | 17 | 0 |
| 1.0% Surfel + Carb. | 21 | 32 | 53 | 46 | 25 | 0 |
| 0.5% Surfel − Carb. | 0 | 5 | 53 | 29 | 12 | 0 |
| 0.7% Surfel − Carb. | 14 | 42 | 31 | 86 | 14 | 0 |
| 1.0% Surfel − Carb. | 39 | 48 | 56 | 38 | 14 | 0 |

It will be apparent to those skilled in the art that various modifications and variations can be made in the processes and products of the present invention. For example, it is anticipated that the degree of seed and plant colonization by the beneficial microorganisms and the percentage of impregnated seeds which germinate can be optimized by those skilled in the art, given the teachings of the instant specification. Thus, it is intended that the present invention cover such modifications and variations, provided that they come within the scope of the appended claims and their equivalents.

What is claimed is:

1. A method for introducing a Clavibacter microorganism into the embryo of a graminaceous, leguminous, or malvaceous seed, comprising the steps of:

adding a Clavibacter microorganism to a biologically compatible liquid carrier to form a suspension of said microorganism in said carrier, imbibing said seed for a time sufficient to allow introduction of said microorganism below the pericarp and into the embryo of said seed, impregnating said imbibed seed with said suspension under conditions sufficient to introduce said microorganism into said embryo, wherein said impregnation is accomplished by a method selected from vacuum infiltration, pressure infiltration, injection, injection followed by vacuum infiltration, and injection followed by pressure infiltration, and removing any excess carrier from said seed while maintaining the viability of said microorganism and said seed.

2. A method for obtaining a plant colonized by a Clavibacter microorganism systemically throughout the plant, wherein the plant and the microorganism co-exist symbiotically, comprising the steps of:

adding a Clavibacter microorganism to a biologically compatible liquid carrier to form a suspension of said microorganism in said carrier, imbibing a graminaceous, leguminous or malvaceous seed for a time sufficient to allow introduction of said microorganism below the pericarp and into the embryo of said seed, impregnating said imbibed seed with said suspension under conditions sufficient to introduce said microorganism into said embryo, wherein said impregnation is accomplished by a method selected from vacuum infiltration, pressure infiltration, injection, injection followed by vacuum infiltration, and injection followed by pressure infiltration, and growing said seed to obtain a plant.

3. A method of claim 2, wherein said seed is a corn, soybean, wheat, rice or cotton seed.

4. A method of claim 1, wherein said seed is a corn, soybean, wheat, rice or cotton seed.

* * * * *